United States Patent [19]

McWhorter et al.

[11] Patent Number: 4,815,477
[45] Date of Patent: Mar. 28, 1989

[54] URINE METER DRAIN CONTAINER WITH LARGE AND SMALL SAMPLE PORTS

[75] Inventors: Daniel M. McWhorter, Lake Bluff; James R. Gross, St. Charles; Carl J. Steigerwald, Fox River Grove, all of Ill.

[73] Assignee: The Kendall Company, Boston, Mass.

[21] Appl. No.: 919,276

[22] Filed: Oct. 15, 1986

[51] Int. Cl.4 .................................................. A61B 5/00
[52] U.S. Cl. ...................... 128/766; 128/767; 604/323; 604/335; 251/4
[58] Field of Search ............... 128/761, 762, 767, 771, 128/764, 766; 604/322, 323, 335, 350, 33, 34, 111, 409, 86, 250; 73/863.86, 864.63, 863.41; 251/7, 4; 222/482; 141/130, 329

[56] References Cited

U.S. PATENT DOCUMENTS

| | | | |
|---|---|---|---|
| 2,471,623 | 5/1949 | Hubbell | 604/250 |
| 3,559,703 | 2/1971 | Maul et al. | 141/329 |
| 3,961,529 | 6/1976 | Hanifl | 128/771 |
| 4,036,210 | 7/1977 | Campbell et al. | 604/33 |
| 4,105,031 | 8/1978 | Kurtz et al. | 604/321 |
| 4,305,403 | 12/1981 | Dunn | 128/767 |
| 4,305,405 | 12/1981 | Meisch | 128/767 |
| 4,460,362 | 7/1984 | Bates | 604/335 |

Primary Examiner—Stephen C. Pellegrino
Assistant Examiner—J. L. Kruter
Attorney, Agent, or Firm—Donald Halgren

[57] ABSTRACT

A urine meter attached to a flexible urine collection bag. The urine meter comprises a rigid container which is dischargeable into the collection bag. A valve is disposed at the bottom of the rigid container to permit small samples to be taken in a sterile, multiple use, manner. The valve also permits large urine samples to be taken from the container, by the release of a bias device on the valve. The large samples are taken infrequently. The small samples are taken from a reusable sampling port which reseals itself when the sampling device, such as a hypodermic needle, is withdrawn.

9 Claims, 2 Drawing Sheets

4,815,477

URINE METER DRAIN CONTAINER WITH LARGE AND SMALL SAMPLE PORTS

BACKGROUND OF THE INVENTION (1) Field of the Invention

The present invention relates to a closed system urinary drainage bag, and more particularly to the drain valve arranged on a urine meter disposed on the front of an urine collection bag.

(2) Prior Art

Urine collection begins after catheterization of a patient, wherein urine drains from the bladder, through a catheter and drainage tube connected to the catheter, and into a urine collection system. The urine collection system generally comprises a urine bag, and a urine meter. A urine collection bag, for example, is shown in U.S. Pat. No. 4,465,484. A urine collection system with a holding chamber and a one way valve is shown in U.S. Pat. No. 4,460,362. These urine collection systems did not fully provide for metering capabilities and which permitted small samples to be taken while limiting the likelihood of retrograde infection or bacterial contamination within the metering chamber.

U.S. Pat. No. 4,305,405 shows a urine collection bag with a meter attached thereto. The meter has a sampling port thereon. The meter however fails to permit samples to be taken from the meter in such a quantity such as 30 to 40 ml. for tests for specific gravity or the like. U.S. Pat. No. 3,683,894 discloses a urine collection bag with a "push-pull" type valve attached to a urine meter therewith. U.S. Pat. No. 4,305,403 shows a valve with a distortable tube for drainage of a meter. However this valve is cumbersome and unweildy in compact situation requirements because its biasing means are arranged on the backside of the valve housing, making a compact design impossible. U.S. patent application Ser. No. 876,622 discloses a meter on a collection bag. The meter has a drain valve wherein fresh urine may be sampled in such quantity as to permit a specific gravity test to be done thereon.

It is an object of the present invention to provide a urine meter with a drain valve thereon which will permit both means for taking small aseptic samples such as with a syringe, while permitting larger volumes to be removed from the urine source i.e., the meter, by opening of the drain valve. It is a further object of the invention to provide sampling ports which will minimize retrograde contamination of the fluid within the meter and hence within the system and ultimately the patient.

SUMMARY OF THE INVENTION

The present invention comprises a multiple sample valve for a combined urine output meter and a drainage bag for collecting, measuring and sampling urine output from a catheterized patient. The present invention permits small samples of fresh urine to be taken from the meter as well as permitting large samples to be taken from the meter when larger volumes of urine are required.

The urine meter comprises a receptacle having a wall defining a cavity and an opening at the top receptacle for communication with the cavity. A valve is disposed at the bottom of the meter body. A conduit is disposed through the bottom of the meter body and is in fluid communication with the valve thereat. The valve comprises a generally longitudinally extending housing having an adapter opening at its upper end into which the conduit extends. The valve has an opening at its lower end. A resilient, flexible tube is disposed within the generally longitudinal housing of the valve and is in overlapping relationship with the adapter which mates with the conduit from the bottom of the meter body. The housing for the valve, has a front side and a back side. A biased slider plunger extends through an opening in the front side of the housing and is movable transversely across the body of the valve. An opening through the slider permits the flexible conduit to pass therethrough. A pair of wall members are disposed on either side of the slider. The wall members define the opening therethrough to permit the flexible conduit to pass. A biasing means such as a spring is disposed against the front wall of the housing and a tab on the distalmost portion of the slider. The spring acts as biasing means which causes the proximal end of the slider to pinch the flexible conduit against a bracket arrangement on the housing and thus close the conduit off.

A sampling port may be disposed in the valve housing between the slider and the body of the urine meter. An opening comprising the port is disposed in the upper half of a front portion of the valve body or housing. A septum, or rubber plug, is disposed over the opening.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
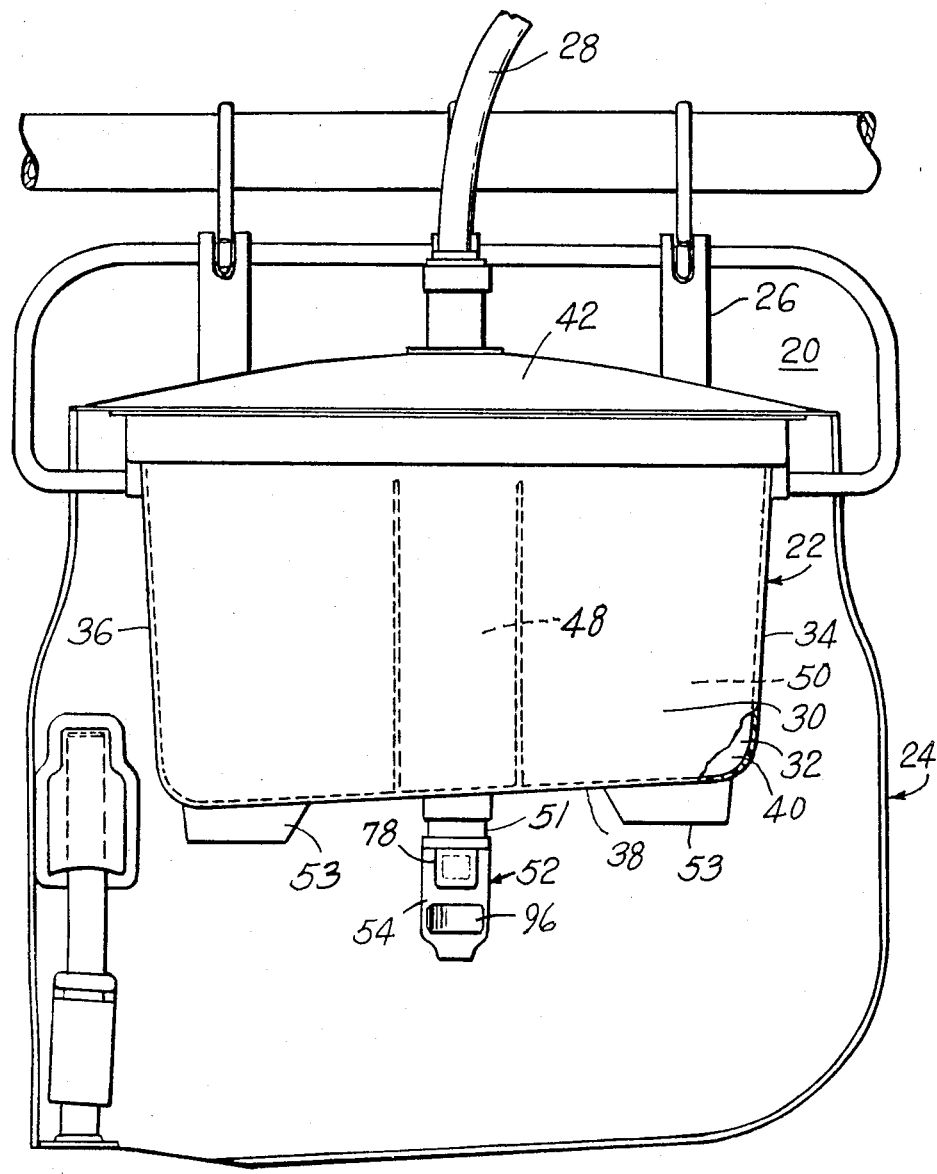
FIG. 1 is a front elevational view of a urine bag assembly having a meter therewith and a valve attached to said meter.

Referring now to the drawings in detail, and particularly to FIG. 1, there is shown a urine collection assembly 20, having a rigid front receptacle 22, a flexible rear container or bag 24, a support arrangement 26, and inlet conduit means 28, similar to that shown in commonly assigned U.S. patent application Ser. No. 876,622 and U.S. patent application Ser. No. 919,290, both incorporated herein by reference. The receptacle 22 may be made of any suitable rigid plastic material which is transparent. The container 24 may have walls constructed of any suitable, flexible plastic material.

The receptacle 22 has a front wall 30, a rear wall 32, a pair of sidewalls 34 and 36 at proposed sides of the receptacle 22, and a bottom wall 38 defining a cavity body in the receptacle 22. The receptacle 22 has a top 42 defining an elongated opening. In use, urine is initially directed into a small inner compartment 48 for more accurate volume measurement by indicia arranged on the front wall 30. Urine s permitted to overflow from the upper portion of the walls defining the inner compartment 48. The receptacle 22 has a pair of lower depending lift tabs 53 to facilitate movement of the receptacle 22 relative to the container 24, for drainage of the contents of the receptacle 22 into the container 24.

Figure 2:
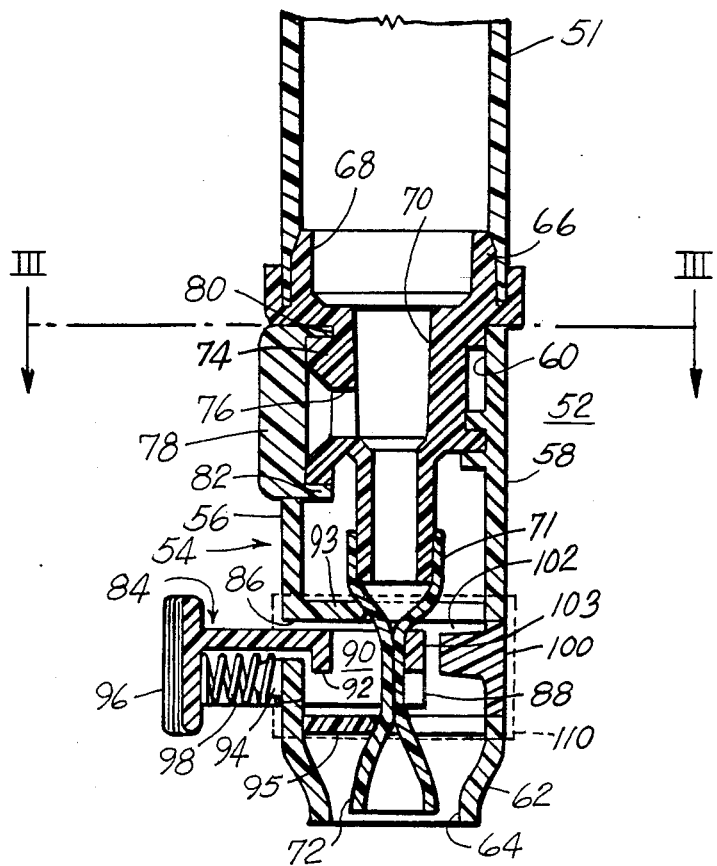
FIG. 2 is a side elevational view of the valve shown in FIG. 1.

The receptacle 22 has a lower valve 52 communicating with the inner compartment 48 through a conduit 51, as shown in FIG. 2, in order to drain urine from the inner compartment 48 during use of the urine meter 20, to obtain either a large or a small fresh sample of urine.

The valve 52 extending beneath receptacle 22 is of generally longitudinal shape, having a housing 54 comprising a front half 56, and a rear half 58. The valve 52 has an upper end with an opening 60 therein. The valve 52 has a lower end 62 with an opening 64 therein. An adapter 66 mates in the opening 60 at the upper end of the valve 52. The adapter 66 is arranged to snugly fit into the configuration of the opening 60. The uppermost proximal end of the adapter 66 has a circular opening 68 theredisposed. The opening 68 in the distal end of the adapter 66 is in fluid communication with a bore 70 which extends completely longitudinally through the adapter 66. The lower end of the adapter 66 is centrally disposed within the housing 54 of the valve 52. The distal most end of the adapter 66 has a U generally cylindrically shaped configuration thereto, which mates with a flexible tubular conduit 71 which itself extends through the generally longitudinal center of the valve member 52. The flexible conduit 71 has an open end 72 which is generally coincidental with the open end of the lower end 62 of the valve 52.

The adapter 66 has a side portion 74 with an opening 76 therein. The opening 76 permits communication between the bore 70 of the adapter 66 from outside thereof.

A septum 78 made of a resilient plastic or rubber material mates over and covers the orifice 76 on the side 74 of the adapter 66, is shown in FIG. 2. The septum 78 is arranged so as to seal the opening 76 from any outside air or contamination and allows penetration by a needle or the like. An annular groove 80 around the side portion 74 on the adapter 66 receives a ridge 82 of the septum 78 to ensure the seal thereinbetween.

A slide release or slider 84 extends through an opening 86 in the front panel 56. The slider 84 is arranged transversely across the longitudinal fluid flow path in the valve 52. The slider 84 has a pair of sidewalls 88, only one shown in FIG. 2 and a pair of transverse walls 92 that extend between the sidewalls 88, which all define an opening 90 disposed therebetween. The flexible conduit or tube 71 is arranged to be disposed within the opening 90 in the slider 84. A pair of brackets 93 and 95 are disposed above and beneath the slider 84, respectively. The brackets 93 and 95 extend only partly transversely across the body of the valve housings 56 and 58. A nub 94 is arranged on the lower outside edge of the opening 86 on the front housing 56. A faceplate 96 is disposed on the distalmost end of the slider 84. A spring 98 is disposed between the back side of the face plate 96 and the nub 94, so as to continuously bias the slider 84 outwardly from the valve 52. The flexible resilient conduit 71 is biased in the pinched closed condition by being pressed against the pair of brackets 93 and 95 on the front half 56 of the housing 54, by the proximalmost wall 92 across the end of the slider 84.

The back half 58 of the housing 54 may have a frangible panel 100 adjacent the slider 84. The panel 100 may have a tab member 102 which extends inwardly towards the center of the valve 52 and near the proximalmost wall 92 of the slider 84.

Figure 3:
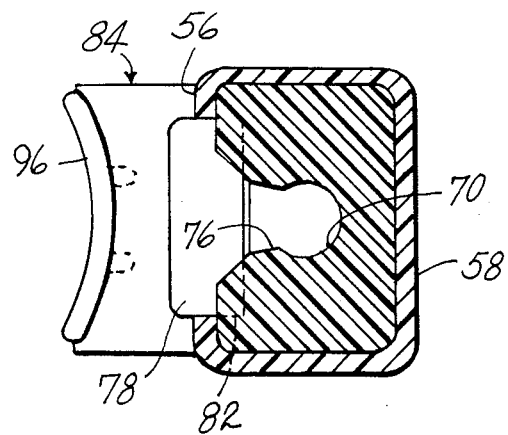
FIG. 3 is a sectional view taken along the lines III—III of FIG. 2.

During use of the urine meter assembly 20, urine is first retained in the receptacle 22 for initial volume measurement thereof. Actual sampling of the urine for further testing will usually be necessary. As is most often the case, only small samples, say in the range of 2 to 10 milliliters are needed. This may be done by inserting a needle syringe through the septum 78 so as to retrieve the fresh urine which is collected within the bore 70 of the valve 52 at the bottom of the receptacle 22. The needle may be merely inserted through the resealable septum 78 through the orifice 76 and the front portion 74 of the adapter 66 until it reaches the bore 70, whereupon the small sample may be taken. The path for this sampling is also shown in FIG. 3 wherein the septum 78 shows access to the orifice 6 and the bore 70 of the valve 52.

When larger urine samples are required to be taken, such as for specific gravity tests of the urine, wherein 30 to 40 milliliters of fresh urine may need to be removed, the slider 84 may be pressed inwardly against the biasing action of the spring 98 so as to open the flexible tube and unpinch it, thus permitting rapid drainage of the rigid receptacle 22. Unfortunately however, this action may permit the possibility of contamination of the rigid receptacle 22. It is important to utilize the slider 84 for taking urine samples as infrequently as possible. It is also very important to know that a large sample has been taken when one actually has been done! Thus the valve opening indication means such as the frangible panel on the back half of the housing 58 may be utilized to show that the slider 84 has been pressed inwardly so as to fracture the frangible panel 100 by pressing against the tab 102 thereof.

A frangible panel would discourage the easy (or lazy) way of taking a small urine sample and make evident the use of such a procedure and indicate the possibility of contamination. The bag or collection system 20 could then be changed or other necessary actions undertaken.

Other slider evident means for valve opening means may be arranged around the valve housing 54 as shown in dashed lines in FIG. 2, such as a heat shrinkable band 110 which may be disposed about the periphery of the valve housing 54 and particularly about the back side of the back half of the housing 58. Thus if the slider 84 were pushed inwardly to open (unpinch) the flexible tubing 71, the tamper evident seal or band 110 would be torn or otherwise disturbed by the back wall 92 of the slider or something in the nature of a boss 105 on the backside of the slider 84 to indicate that the valve had been opened for flow of urine samples therethrough.

One further embodiment of this urine collection bag assembly comprises the aforementioned valve 52 without the small sampling means or septum 78 in the valve housing 56.

Thus there has been shown a novel arrangement for permitting small fresh samples to be taken from a urine meter, while also permitting larger fresh urine samples to be taken as required. The large sampler means however having utilization discouraging means therewith in order to inhibit medical personnel from taking small samples from the large sampler means which would possibly otherwise promote the possibility of contamination within the entire system.

We claim:

1. A urine meter comprising:
   a receptacle having a wall defining a cavity for receiving a supply of urine therein;
   a valve disposed in fluid communication with said receptacle, said valve having a housing which contains both a piercable small sample obtaining means and a separate larger sample obtaining means therein, to permit either size sample to be taken directly with drawn from said urine receptacle through said valve housing;

said large sample means, having biased release means on the front side of said housing, adjacent and downstream of said piercable small sample obtaining means, comprising a flexible tube being distortable against said housing by said bias release means to permit the stoppage or discharge of said large urine samples from said housing.

2. A urine meter as recited in claim 1, wherein said biased release means comprises a slider having a transverse wall to press against and pinch said flexible tube.

3. A urine meter as recited in claim 2, wherein said housing has a cross bracket arrangement disposed about an opening, said slider being movably disposed through said opening, said cross bracket arrangement comprising said portion of said housing against which said flexible tube is pressed by said transverse wall on said slider.

4. A urine meter as recited in claim 2, wherein said biased release means includes a spring which is arranged against the front side of said housing to keep a constant outward pressure on said slider and said flexible tube pinched thereby.

5. A urine meter as recited in claim 2, wherein said housing includes a discharge orifice at one end.

6. A urine meter as recited in claim 5, wherein said adapter has a central channel which is in fluid communication with said sampling port and said flexible tube.

7. A urine meter as recited in claim 2, wherein said housing includes an adapter to mate with the upstream end of said housing, and said adapter comprises said sampling port in said housing.

8. A urine collection bag having a valve arrangement in a valve housing, which valve permits both small asceptical samples and large samples of fresh urine to be taken prior to containment in said collection bag; said valve comprising a first sampling means in said housing having a piercable port disposed in said housing for penetration by a sampling needle' and a second sampling means having a distortable conduit also arranged within said housing, downstream of and in fluid communication with said housing, said distortable conduit being openable and closable by pinching and unpinching said conduit against a wall of said valve housing to permit drainage of a large urine sample through said housing.

9. A urine collection bag as recited in claim 8 wherein said piercable port comprises a resilient self-sealing material disposed in said housing.

* * * * *